(12) United States Patent
Staid et al.

(10) Patent No.: US 7,951,107 B2
(45) Date of Patent: May 31, 2011

(54) MEDICAL DEVICE WITH HIGH PRESSURE QUICK DISCONNECT HANDPIECE

(75) Inventors: Kevin P. Staid, Lowell, MA (US); Mark C. Ettinger, Lexington, MA (US); Brian G. Connor, Newfields, NH (US); Roger Greeley, Portsmouth, NH (US)

(73) Assignee: HydroCision, Inc., North Billerica, MA (US)

( * ) Notice: Subject to any disclaimer, the term of this patent is extended or adjusted under 35 U.S.C. 154(b) by 1421 days.

(21) Appl. No.: 11/193,225

(22) Filed: Jul. 29, 2005

(65) Prior Publication Data

US 2005/0267443 A1 Dec. 1, 2005

Related U.S. Application Data

(62) Division of application No. 10/215,209, filed on Aug. 8, 2002, now Pat. No. 6,923,792.

(60) Provisional application No. 60/310,807, filed on Aug. 8, 2001.

(51) Int. Cl.
*A61M 1/00* (2006.01)
(52) U.S. Cl. ........................................................ 604/34
(58) Field of Classification Search .............. 604/30–34, 604/167.01–167.06, 6.1, 9, 99.02, 99.03, 604/99.04, 236, 247, 288.03
See application file for complete search history.

(56) References Cited

U.S. PATENT DOCUMENTS

| | | | |
|---|---|---|---|
| 1,128,755 A | 2/1915 | Carlson | |
| 1,773,629 A | 8/1930 | Millmine | |
| RE24,329 E | 6/1957 | Booth | |
| 2,808,302 A | 10/1957 | Bowerman | |
| 2,885,227 A | 5/1959 | Burger | |
| 2,937,444 A | 5/1960 | Kern | |
| 3,310,283 A | 3/1967 | Carlton | |
| 3,456,915 A | 7/1969 | Smolen | |
| 3,583,710 A | 6/1971 | Burelle | |
| 3,590,813 A | 7/1971 | Roszyk | |
| 3,620,653 A | 11/1971 | Gaylord et al. | |
| 3,771,907 A | 11/1973 | Neumann et al. | |
| 3,818,913 A | 6/1974 | Wallach | |
| 3,835,858 A | 9/1974 | Hagen | |
| 3,930,505 A | 1/1976 | Wallach | |

(Continued)

FOREIGN PATENT DOCUMENTS

DE 3421 390 A1 12/1985

(Continued)

OTHER PUBLICATIONS

Baer et al., "Jet-cutting—an alternative to the ultrasonic aspirator!" Chirurg, 61:735, 1990 and Reply to commentary.

(Continued)

*Primary Examiner* — Manuel A Mendez
(74) *Attorney, Agent, or Firm* — McCarter & English, LLP

(57) ABSTRACT

A method and apparatus are provided for quickly connecting a handpiece to a pressurized fluid source. A hollow tube on the handpiece is inserted through an aperture in an annular gasket which is held in a chamber in a body. On application of pressurized fluid to the body, the gasket is pressed against the walls of the chamber, and against the tube, thereby channeling the pressurized fluid through the hollow tube. The handpiece is retained in connection with the body by a releasable connector, such as a latch. The handpiece can be removed and replaced by releasing and remaking the connection.

21 Claims, 8 Drawing Sheets

U.S. PATENT DOCUMENTS

| | | | |
|---|---|---|---|
| 3,989,283 | A | 11/1976 | Pepper |
| 3,994,208 | A | 11/1976 | Boyer |
| 4,116,452 | A | 9/1978 | Schanz |
| 4,155,559 | A | 5/1979 | Sieghartner |
| 4,165,084 | A | 8/1979 | Kempf |
| 4,196,909 | A | 4/1980 | Porsch et al. |
| 4,214,507 | A | 7/1980 | Hock et al. |
| 4,235,595 | A | 11/1980 | Arnegger |
| 4,270,440 | A | 6/1981 | Lewis, II |
| 4,281,590 | A | 8/1981 | Weaver |
| 4,336,946 | A | 6/1982 | Wheeler |
| 4,465,438 | A | 8/1984 | Brauer et al. |
| 4,517,977 | A | 5/1985 | Frost |
| 4,521,027 | A | 6/1985 | Marshall |
| 4,560,373 | A | 12/1985 | Sugino et al. |
| 4,601,235 | A | 7/1986 | Roberts |
| 4,690,672 | A | 9/1987 | Veltrup |
| 4,705,038 | A | 11/1987 | Sjostrom et al. |
| 4,730,550 | A | 3/1988 | Bramstedt et al. |
| 4,735,129 | A | 4/1988 | Sjoberg |
| 4,743,033 | A | 5/1988 | Guess |
| 4,761,039 | A | 8/1988 | Hilaris |
| 4,776,616 | A | 10/1988 | Umehara et al. |
| 4,776,769 | A | 10/1988 | Hilaris |
| 4,795,217 | A | 1/1989 | Hilaris |
| 4,798,339 | A | 1/1989 | Sugino et al. |
| 4,798,589 | A | 1/1989 | Tseo |
| 4,811,902 | A | 3/1989 | Nagata |
| 4,813,343 | A | 3/1989 | Schaefer |
| 4,818,190 | A | 4/1989 | Pelmulder et al. |
| 4,827,679 | A | 5/1989 | Earle, III |
| 4,872,813 | A | 10/1989 | Gorton et al. |
| 4,898,574 | A | 2/1990 | Uchiyama et al. |
| 4,913,698 | A | 4/1990 | Ito et al. |
| 4,932,114 | A | 6/1990 | Morse et al. |
| 4,937,985 | A | 7/1990 | Boers et al. |
| 4,940,399 | A | 7/1990 | Gorton et al. |
| 4,950,238 | A | 8/1990 | Sullivan |
| 5,002,316 | A | 3/1991 | Chohan |
| 5,006,043 | A | 4/1991 | Katsumata et al. |
| 5,011,468 | A | 4/1991 | Lundquist et al. |
| 5,018,670 | A | 5/1991 | Chalmers |
| 5,037,431 | A | 8/1991 | Summers et al. |
| 5,052,624 | A | 10/1991 | Boers et al. |
| 5,074,862 | A | 12/1991 | Rausis |
| 5,087,056 | A | 2/1992 | Baglin |
| 5,092,744 | A | 3/1992 | Boers |
| 5,125,582 | A | 6/1992 | Surjaatmadja et al. |
| 5,133,687 | A | 7/1992 | Malloy |
| 5,135,482 | A | 8/1992 | Neracher |
| 5,162,016 | A | 11/1992 | Malloy |
| 5,171,045 | A | 12/1992 | Pasbrig |
| 5,195,754 | A | 3/1993 | Dietle |
| 5,197,955 | A | 3/1993 | Stephens et al. |
| 5,205,779 | A | 4/1993 | O'Brien et al. |
| 5,211,633 | A | 5/1993 | Stouder et al. |
| 5,217,465 | A | 6/1993 | Steppe |
| 5,230,443 | A | 7/1993 | Du |
| 5,250,065 | A | 10/1993 | Clement et al. |
| 5,252,044 | A | 10/1993 | Raines et al. |
| 5,259,842 | A | 11/1993 | Plechinger et al. |
| 5,261,883 | A | 11/1993 | Hood et al. |
| RE34,556 | E | 3/1994 | Sjostrom et al. |
| 5,290,245 | A | 3/1994 | Dennis |
| 5,300,036 | A * | 4/1994 | Mueller et al. ........... 604/167.06 |
| 5,300,046 | A * | 4/1994 | Scarfone et al. ............. 604/264 |
| 5,314,375 | A | 5/1994 | O'Brien et al. |
| 5,322,504 | A | 6/1994 | Doherty et al. |
| 5,364,234 | A | 11/1994 | Eickmann |
| 5,370,609 | A | 12/1994 | Drasler et al. |
| 5,392,694 | A | 2/1995 | Muller et al. |
| 5,423,752 | A | 6/1995 | Haber et al. |
| 5,468,028 | A | 11/1995 | Olson |
| 5,474,336 | A | 12/1995 | Hoff et al. |
| 5,480,163 | A | 1/1996 | Miser et al. |
| 5,482,297 | A | 1/1996 | Burns et al. |
| 5,490,680 | A | 2/1996 | Patel et al. |
| 5,496,267 | A | 3/1996 | Drasler et al. |
| 5,509,911 | A | 4/1996 | Cottone, Sr. et al. |
| 5,511,464 | A | 4/1996 | Cezanne et al. |
| 5,511,830 | A | 4/1996 | Olson et al. |
| 5,533,879 | A | 7/1996 | Chen |
| 5,540,568 | A | 7/1996 | Rosen et al. |
| 5,551,448 | A | 9/1996 | Matula et al. |
| 5,558,646 | A | 9/1996 | Roche |
| 5,562,186 | A | 10/1996 | Osenbaugh |
| 5,562,640 | A | 10/1996 | McCabe et al. |
| 5,607,391 | A | 3/1997 | Klinger et al. |
| 5,624,395 | A * | 4/1997 | Mikhail et al. ............. 604/99.04 |
| 5,626,072 | A | 5/1997 | Mirand et al. |
| 5,711,151 | A | 1/1998 | Engfer |
| 5,713,878 | A | 2/1998 | Moutafis et al. |
| 5,735,815 | A | 4/1998 | Bair |
| 5,749,885 | A | 5/1998 | Sjostrom et al. |
| 5,785,675 | A | 7/1998 | Drasler et al. |
| 5,842,701 | A | 12/1998 | Cawthorne et al. |
| 5,849,023 | A | 12/1998 | Mericle |
| 5,865,442 | A | 2/1999 | Iwashita |
| 5,871,462 | A | 2/1999 | Yoder et al. |
| 5,941,162 | A | 8/1999 | Kiesel |
| 5,944,686 | A | 8/1999 | Patterson et al. |
| 5,960,700 | A | 10/1999 | Staggs et al. |
| 6,017,354 | A | 1/2000 | Culp et al. |
| 6,083,189 | A | 7/2000 | Gonon et al. |
| 6,085,631 | A | 7/2000 | Kownacki |
| 6,142,484 | A | 11/2000 | Valls, Jr. |
| 6,161,834 | A | 12/2000 | Pollack et al. |
| 6,216,573 | B1 | 4/2001 | Moutafis et al. |
| 6,280,302 | B1 | 8/2001 | Hashish et al. |
| 6,346,093 | B1 * | 2/2002 | Allman et al. ........... 604/167.06 |
| 6,375,635 | B1 | 4/2002 | Moutafis et al. |
| 6,419,654 | B1 | 7/2002 | Kadan |
| 6,451,017 | B1 | 9/2002 | Moutafis et al. |
| 6,464,567 | B2 | 10/2002 | Hashish et al. |
| 6,511,493 | B1 | 1/2003 | Moutafis et al. |
| 6,669,710 | B2 | 12/2003 | Moutafis et al. |
| 6,899,712 | B2 | 5/2005 | Moutafis et al. |
| 6,923,792 | B2 | 8/2005 | Staid et al. |
| 6,960,182 | B2 | 11/2005 | Moutafis et al. |
| 2001/0002562 | A1 | 6/2001 | Moutafis et al. |
| 2002/0050197 | A1 | 5/2002 | Moutafis et al. |
| 2002/0176788 | A1 | 11/2002 | Moutafis et al. |
| 2002/0177802 | A1 | 11/2002 | Moutafis et al. |
| 2003/0055404 | A1 | 3/2003 | Moutafis |
| 2003/0083681 | A1 | 5/2003 | Moutafis et al. |
| 2003/0125660 | A1 | 7/2003 | Moutafis et al. |
| 2004/0228736 | A1 | 11/2004 | Moutafis et al. |
| 2004/0230211 | A1 | 11/2004 | Moutafis et al. |
| 2004/0234380 | A1 | 11/2004 | Moutafis et al. |
| 2004/0243157 | A1 | 12/2004 | Connor et al. |

FOREIGN PATENT DOCUMENTS

| | | |
|---|---|---|
| DE | 225 618 A1 | 8/1988 |
| EP | 0 411 170 A1 | 2/1991 |
| EP | 0 485 133 A1 | 5/1992 |
| EP | 0 489 496 A1 | 6/1992 |
| EP | 0 551 920 A1 | 7/1993 |
| EP | 0 855 507 A | 7/1998 |
| FR | 1 241 277 A | 9/1960 |
| FR | 2 094 507 A | 2/1972 |
| GB | 199057 | 6/1923 |
| GB | 617567 | 2/1949 |
| GB | 651836 A | 4/1951 |
| JP | 38-26972 | 12/1963 |
| JP | 40-4710 | 3/1965 |
| JP | 45-14746 | 5/1970 |
| WO | WO 94/14584 A1 | 7/1994 |
| WO | WO 99/33510 | 7/1999 |
| WO | WO 2004/069064 | 8/2004 |

OTHER PUBLICATIONS

Baer et al., "New water-jet dissector: initial experience in hepatic surgery," Br. J. Surg., vol. 78, pp. 502-503, Apr. 1991.

Baer et al., "Water-jet dissection in hepatic surgery," Minimally Invasive Therapy, vol. 1, pp. 169-172, 1992.

Baer et al., "Hepatic Surgery Facilitated by a New Jet Dissector," HPB Surgery, vol. 4, pp. 137-146, 1991.

Baer et al., "Subtotal hepatectomy; a new procedure based on the inferior right hepatic vein" Br. J. Surg. 1991 78:1221-1222.

Field, J.E, "The physics of liquid impact, shock wave interactions with cavities, and the implications to shock wave lithotripsy," Phys. Med. Biol., vol. 36, No. 11, pp. 1475-1484, 1991.

Giraud et al., "Bone cutting," Clin. Phys. Physiol. Meas., vol. 12, No. 1, pp. 1-19, 1991.

Izumi et al., "Hepatic resection using a water jet dissector," Surgery Today Jpn. J. Surg., vol. 23, pp. 31-35, 1993.

Terzis et al., "A new system for cutting brain tissue preserving vessels: water jet cutting," British Journal of Neurosurgery, vol. 3, pp. 361-366, 1989.

Tikhomiroy, R.A., et al "High-Pressure Jet Cutting TJ840 G5313" 1992.

Zhong et al., "Propagation of shock waves in elastic solids caused by cavitation microjet impact. II: Application in extracorporeal shock wave lithotripsy," J. Acoust. Soc. Am., vol. 94, No. 1, pp. 29-36, Jul. 1993.

International Search Report Nov. 4, 2002 of U.S. PCT 2002/13608.

International Search Report Dec. 10, 2002 of U.S. PCT 2002/25133.

Communication pursuant to Article 96(2) EPC, dated Aug. 29, 2005 for corresponding European patent application serial No. 02768451.3-2310.

Communication for corresponding Canadian patent application serial No. 2,493,238, dated Jun. 17, 2005.

Communication for corresponding Australian patent application serial No. 2002331012, dated Feb. 14, 2005.

Examination report for corresponding Japanese Patent Application No. 2003-518645.

Examiner's Report for corresponding Canadian Patent Application No. 2,493,238 dated Mar. 13, 2006.

* cited by examiner

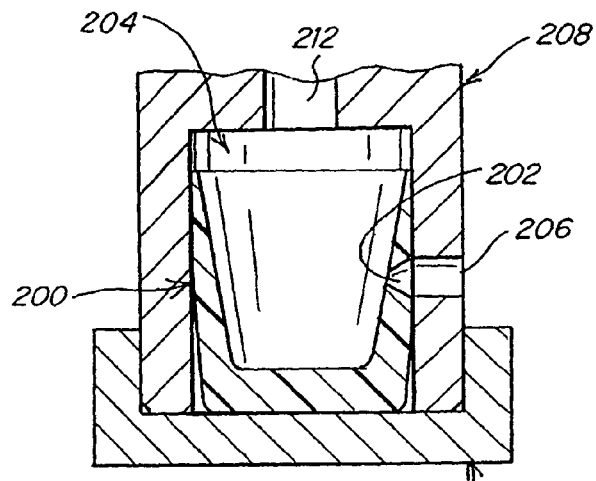
Fig. 3a
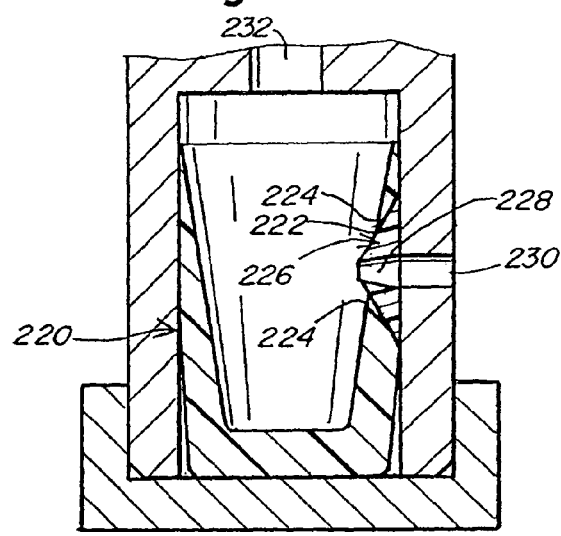
Fig. 3b1
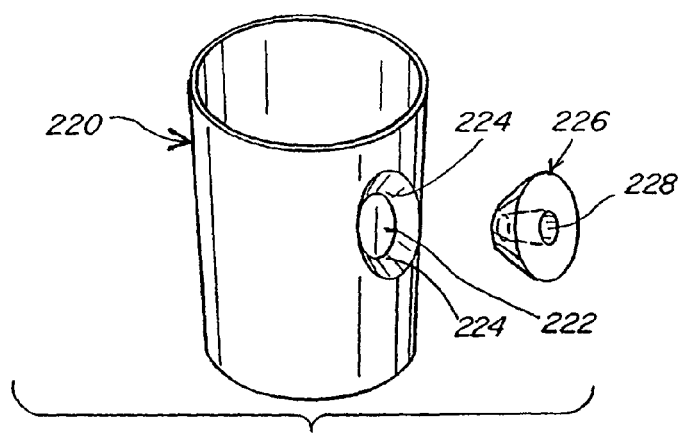
Fig. 3b2

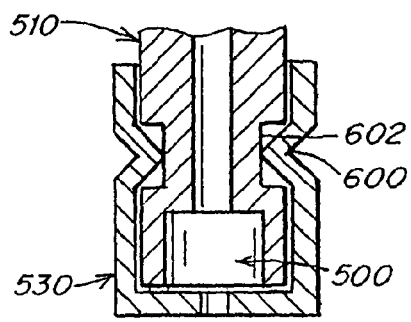
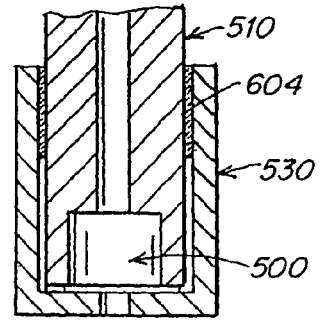
Fig. 7a  Fig. 7b
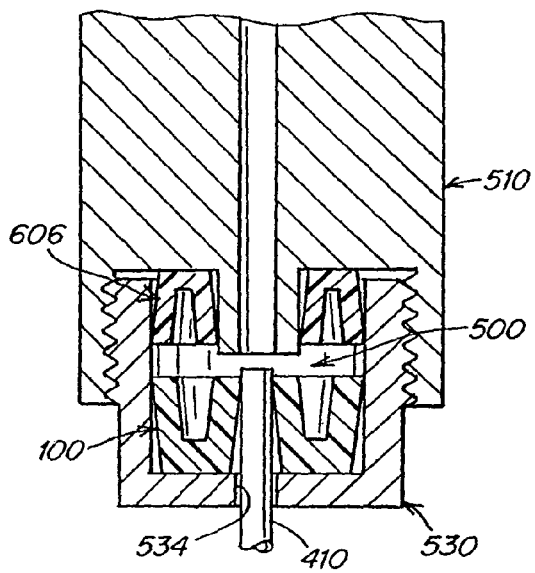
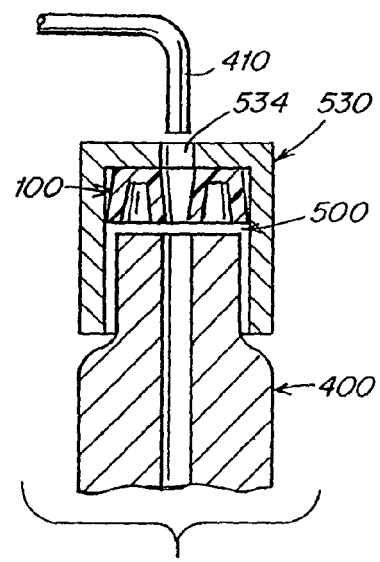
Fig. 8a  Fig. 8b
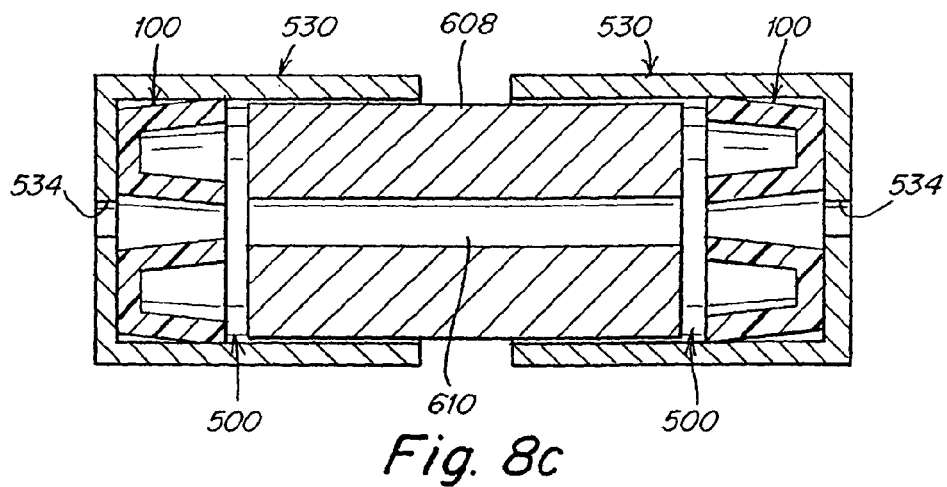
Fig. 8c

US 7,951,107 B2

MEDICAL DEVICE WITH HIGH PRESSURE QUICK DISCONNECT HANDPIECE

RELATED APPLICATIONS

The present patent application is a division of U.S. application Ser. No. 10/215,209, filed Aug. 8, 2002 and issued as U.S. Pat. No. 6,923,792 on Aug. 2, 2005, which claims priority to U.S. Provisional Patent Application No. 60/310,807, filed Aug. 8, 2001, each of which is incorporated herein by reference.

FIELD OF THE INVENTION

The present application relates to a device that facilitates connection of a source of high pressure fluid to the operating portion of various medical instruments. The device is particularly useful in instruments, including those of the disposable variety, in which a high pressure fluid jet is used in the treatment of tissue.

BACKGROUND OF THE INVENTION

Jets of high pressure fluids, such as saline, have been used in various surgical and medical applications to, for example, remove tissue, debride wounds, and drive small burrs and cutters. Such uses are described in U.S. Pat. Nos. 5,713,878, 5,871,462, 5,944,686, and 6,216,573, owned by the assignee of the present application, as well as in patents to others.

Devices using these water jets typically have two principal subsystems. One part compresses the fluid to high pressure, at least about 500 to 1,000 pounds-per-square inch (psi), and more typically from about 1,000 to 25,000 psi or more, with a preferred range, dependent on the end use of the device, that will often be narrower, such as 6,000 to 15,000 psi, 3,000 to 12,000 psi, or 10,000 to 20,000 psi. (1000 psi is about 7 MPa.) The pressurized fluid is conveyed through flexible tubing to a handpiece, which may utilize the pressurized fluid in various ways. For example, the handpiece may permit the surgeon to direct a stream of fluid at tissue, such as in a tissue removal or debriding operation, or it may use the stream of fluid to drive a rotating burr or cutter. Typically, the handpiece and tubing are sterile, while the pump is internally sterile but located outside of the sterile field. In some applications, the handpiece may be disposable, as cleaning after an operation is not necessarily reliable.

Many prior art methods for connecting high-pressure liquid streams involve tightening screw connections, typically in order to compress and deform gaskets. Gaskets in a high-pressure system can be problematic, because, to the extent that they are elastomeric, they tend to deform and extrude, while stiffer ones may not seal well.

Medical procedures often require the use of more than one type of handpiece. It is therefore useful to be able to detach the handpiece from the high-pressure supply and change the handpiece during a procedure. This procedure requires simplicity of operation in a sterile field, and preferably does not involve manipulations difficult to conduct with gloved hands. At the same time, the connection must be able to sustain high pressures as described above without leaking. Any such mechanism preferably is inexpensive, so as to be disposable, and it should be sterilizable.

SUMMARY

The present invention provides a high-pressure connection suited for use in medical systems employing high pressure fluids, particularly liquids. In some of these applications, jets of liquid, such as isotonic saline, are used, for example, to cut tissue, to debride wounds, to lavage, to disinfect, to wash tissue surfaces, and to provide power to devices, for example by driving a turbine. Each different medical application may require a particular form of handpiece optimized for the particular procedure, or may require a family of handpieces. In the course of a medical procedure, it may be useful to use several different handpieces, and perhaps to use a particular handpiece at different times during the procedure. In one aspect, the present invention provides a system that permits changing of the handpieces used during a single medical procedure.

A physician, once scrubbed and gowned and present in a surgical field, needs to be able to execute changes of handpieces without removing gloves or leaving the field, making simplicity of connection and disconnection critical. In another aspect, the invention provides a means by which a single pump or other source of high pressure fluid may be easily connected and disconnected to one or more handpieces during the course of a procedure.

It is also advantageous to be able to use a single high-pressure fluid source sequentially for more than one patient without requiring it to be sterilized between patients. This can be a significant source of savings when the same procedure, decubitus ulcer treatment, for example, is to be performed on multiple patients during the course of a day. In another aspect of the invention, the high-pressure connection facilitates such sequential use.

Various handpieces may also include low-pressure return lines or other conduits that may need to be safely and quickly disconnected when changing handpieces. In another aspect, the invention provides a means for quick connection or disconnection of such auxiliary conduits.

In another aspect of the invention, a high pressure connection includes a gasket that, when compressed by the pressure of fluid flowing through the device, forms a tight seal that prevents the fluid from passing between the gasket and adjacent surfaces.

In another aspect of the invention, a high pressure connection is constructed such that a component of the force resulting from the pressurized fluid operates on a gasket in a direction normal to the direction of fluid flow, so as to form a tight seal that prevents the fluid from passing between the gasket and adjacent surfaces.

In another aspect of the invention, a gasket is annular in shape and is adapted to receive a supply tube through a hole in its center. The annular gasket has an annular channel in an axial surface constructed to direct a component of the force directed on the gasket in approximately radial directions inwardly and outwardly, so as to form a tight seal that prevents the fluid from passing between the gasket and adjacent surfaces.

In another aspect of the invention, a high pressure connection includes a body and a cap, where a gasket fits into a recess in the body and the cap fits over the body.

In another aspect of the invention, a medical device has a high pressure fluid connection with (a) a first lumen adapted for fluid flow, (b) a second lumen adapted for fluid flow and arranged at least partially within the first lumen, and (c) a gasket positioned between the first lumen and the second lumen and constructed and arranged such that the pressure of the fluid flowing though the connection creates fluid impermeable seals between the gasket and the first lumen and between the gasket and the second lumen.

In another aspect of the invention, a medical device has a quickly changeable connection between a high pressure fluid source and a handpiece, wherein the connection comprises (a) a thin tube having a lumen in fluid connection with a first fluid pathway extending through the handpiece, (b) a chamber having a first opening receiving the thin tube and a second opening connecting to a second fluid pathway, (c) a gasket located in the chamber and having a base disposed adjacent to the first opening and a passage through the base surrounding the thin tube, wherein the gasket has a first rim contacting the wall of the chamber and a second rim contacting the thin tube, and (d) a latching mechanism to maintain the tube in the gasket.

In another aspect of the invention, a system for quickly changing handpieces attached to a high pressure fluid source includes (a) at least one handpiece carrying a portion of a latching mechanism and one of a connecting tube and a chamber having an aperture leading to a gasket, and (b) a high pressure fluid source carrying a complementary portion of a latching mechanism and the other of a connecting tube and a chamber having an aperture leading to a gasket, wherein the gasket has an inner rim and an outer rim and the inner and outer rims engage the connecting tube and the wall of the chamber, respectively, when the connecting tube is inserted in the chamber and pressure is applied to the chamber.

In another aspect of the invention, a medical instrument for performing surgery using a high pressure fluid jet is improved by the addition of a handpiece that is readily connected and disconnected from the source of high pressure fluid, wherein the means of connection is formed by (a) an inlet tube connected to the handpiece, (b) a gasket with inner and outer rims projecting inwardly and outwardly, respectively, with respect to the base, and (c) a chamber for holding the gasket, the chamber being connected to the source of high pressure fluid and having an aperture in alignment with the hole in the gasket. The projections of the inner and outer rims of the gasket are adapted to seal the joints between the gasket and an inner wall of the chamber and between the gasket and the inlet tube. The connection may be made by inserting the inlet tube through the aperture in the chamber and the hole in the gasket, and the connection may be maintained by the engagement of reversible latching means.

In another aspect of the invention, a method for ensuring accurate mating of at least one tube in a handpiece with a corresponding gasket in a connector includes providing corresponding keying features on the handpiece and the connector, and providing a sufficient depth of travel of the connector within the handpiece before contact between the tube and the gasket to ensure angular alignment between the tube and the gasket.

In another aspect of the invention, a high-pressure fluid connection in a surgical instrument or system comprises (a) a chamber containing a high pressure fluid from a fluid source, the chamber having an inner surface; (b) a tube communicating with the chamber for conducting the fluid to the surgical instrument or system, the tube having an outer surface and a central axis; and (c) a gasket surrounding the tube and coupling the tube to the chamber to provide a seal between the inner surface of the chamber and the outer surface of the tube, wherein the gasket includes a central channel for receiving the tube; and an annular channel surrounding the central channel, the annular channel being formed by inner and outer side walls that are disposed at an acute angle with respect to the central axis of the tube and wherein the inner and outer side walls extend away from one another from a closed end to an open end.

In another aspect of the invention, a method for conducting a surgical procedure requiring the use of a high pressure fluid jet applied to more than one exchangeable handpiece includes (a) providing a handpiece that is reversibly connectable to a source of high pressure fluid, wherein the reversible connection is made by the insertion of a tube into a chamber containing a gasket that has an inner rim, an outer rim, and a passage for the tube, wherein the gasket deforms as a result of the pressure of the fluid sufficiently to block the passage of fluid out of the chamber except via the tube, and (b) maintaining the connection between the handpiece and the source of high pressure fluid by releasable latching means.

The success of this simple device is surprising. In contrast to prior art devices, the gasket of the inventive device has no place into which it can extrude, and its deformation by pressure tends to increase the tightness of the sealing.

BRIEF DESCRIPTION OF THE DRAWINGS

The objects, advantages and features of this invention will be more clearly appreciated from the following detailed description, when taken in conjunction with the accompanying drawings, in which:

FIG. 2b is a top plan view of the gasket of FIG. 2a;

FIG. 2c is cross-sectional view of the gasket of FIG. 2a;

FIG. 3a is cross-sectional view of an alternative chamber assembly according to the present invention;

FIG. 3b shows cross-sectional and perspective views of an alternative chamber assembly according to the present invention;

FIG. 3c shows cross-sectional and top plan views of an alternative gasket according to the present invention;

FIG. 3d shows cross-sectional and perspective views of an alternative gasket according to the present invention;

FIG. 4b is a cross-sectional view of the cap of FIG. 4a;

FIG. 5a is an end view of a stem according to the present invention;

FIG. 5b is a cross-sectional view the stem of FIG. 5a;

FIG. 7a is a cross-sectional view of an alternative means of binding a cap to a stem according to the present invention;

FIG. 7b is a cross-sectional view of a second alternative means of binding a cap to a stem according to the present invention;

FIG. 8a is a cross-sectional view of an alternative chamber according to the present invention;

FIG. 8b is a cross-sectional view of a second alternative chamber according to the present invention;

FIG. 8c is a cross-sectional view of a third alternative chamber according to the present invention;

DETAILED DESCRIPTION

Figure 1:
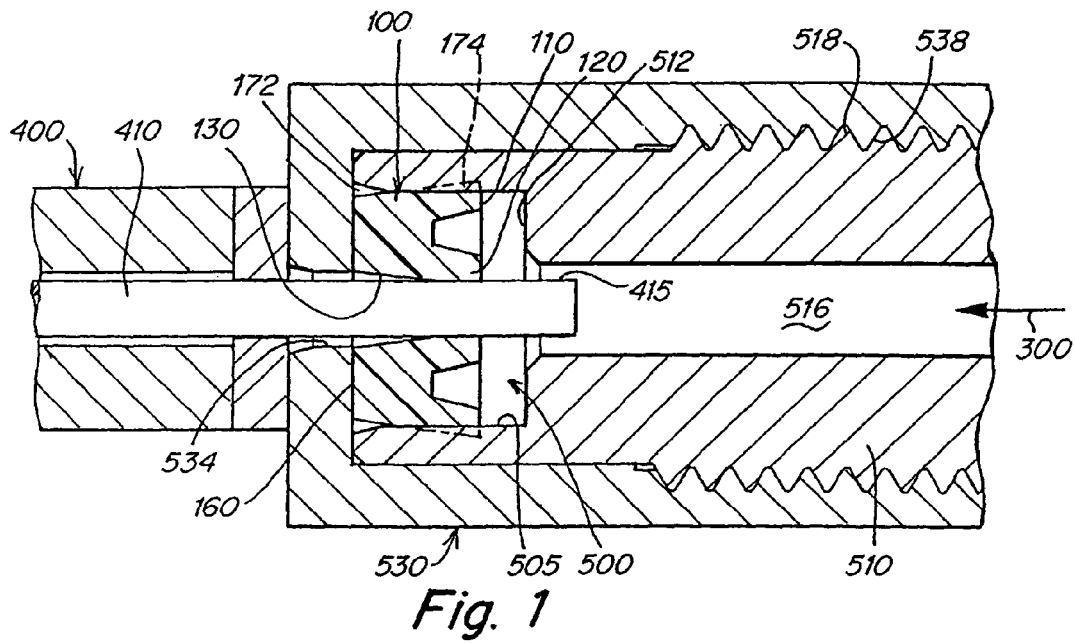
FIG. 1 is a partial schematic diagram of a high pressure connection according to the present invention.

The invention will now be described with particular reference to FIG. 1, which shows an illustrative embodiment in which a connection device mates a high pressure fluid source 300 with a handpiece 400. This embodiment includes a gasket 100 that is disposed in an opening 512 in a stem 510 onto which is mounted a cap 530, such as by the use of threads 518, 538. The gasket 100 receives a handpiece supply tube 410 through its center. As described more fully below, the pressure of the fluid flowing from the high pressure fluid source 300 presses the outer surfaces of the gasket 100 against the inner wall 505 of the chamber 500 and against the outside wall 415 of the handpiece supply tube 410, thereby preventing the fluid from passing between the gasket 100 and the inner wall 505 or between the gasket 100 and wall 415 the handpiece supply tube 410.

FIG. 2 shows three different illustrative embodiments of a gasket 100 according to the invention. FIGS. 2a, 2b, and 2c are a perspective view, a face-on view, and a cross-sectional view, respectively, of a first embodiment of the gasket 100. The annular gasket 100 of this first embodiment includes an outer rim 110, an inner rim 120 surrounding a central hole 130, and a base portion 140. The inner and outer rims 110, 120 form an annular channel 150. Hole 130 serves as an opening for insertion of the handpiece supply tube 410 and preferably is shaped so that, upon pressurization of the chamber 500 or equivalent, the gasket 100 is pressed against the handpiece supply tube 410 in a manner that substantially prevents egress of fluid around the gasket 100. In addition, the gasket 100, or another gasket, seals the chamber 500 so that pressurized fluid cannot flow between the gasket 100 and the inner wall 505 of the chamber 500.

Figure 2A:
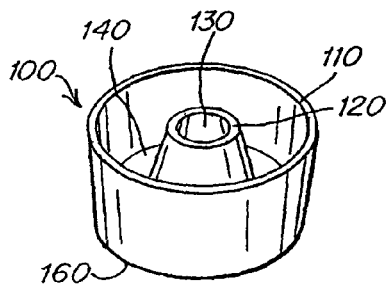
FIG. 2a is a perspective view of a gasket according to the present invention.
Figure 2B:
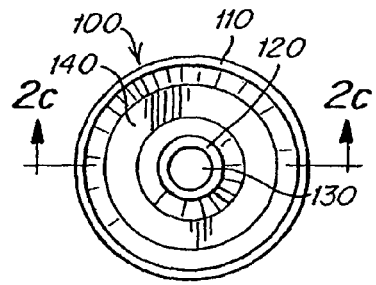
Figure 2C:
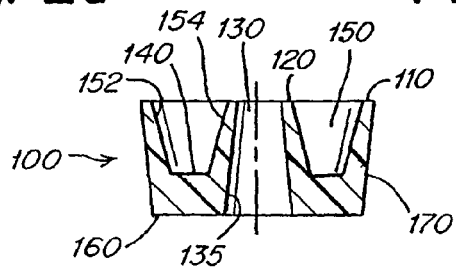

The side walls 152 and 154 of the channel 150 of this embodiment preferably form acute angles with respect to a central axis of hole 130 or with respect to a flow of fluid through hole 130. Outer walls 152 preferably flare or extend radially outwardly from base portion 140 to a top of gasket 100, while inner walls 154 preferably flare or extend radially inwardly from base portion 140 to a top of gasket 100, as shown in FIG. 2c. This construction allows a component of the pressure associated with the flow of fluid through chamber 500 to operate on the gasket 100 in a direction normal to the flow of fluid, forcing the inner and outer rims 110, 120 against walls 505 and 415, thereby preventing fluid from flowing between the gasket 100 and adjacent surfaces. It should be understood however, that while such radial flaring of the walls of the channel 150 has been found to be advantageous, the device can function without such an arrangement.

The inner surface 135 of the central hole 130 of this embodiment preferably flares or extends radially inwardly from the bottom 160 to the top of the gasket 100, and the outside surface 170 of the gasket 100 preferably flares or extends radially outwardly from bottom 160 to the top of gasket 100, as shown in FIG. 2c. Walls 135 and 170 both preferably form acute angles with respect to the central axis of hole 130 or with respect to the flow of a fluid through hole 130. The flaring of the outside surface 170 of the gasket 100 is illustrated in FIG. 1 by a gap 172 between the base portion 140 of the gasket 100 and the inner wall 505, and as an overlap 174 of the rim 110 and the inner wall 505. This arrangement ensures that the inner rim 120 is in contact with wall 415 of the handpiece supply tube 410 and, similarly, ensures contact between the outer surface of wall 170 of gasket 100 and the inner walls 505 of the chamber 500. It should be appreciated, however, that the device can function without such an arrangement.

Figure 2D:
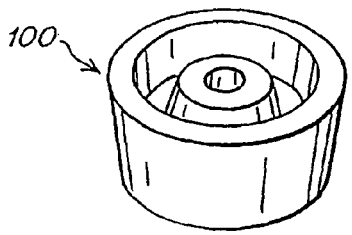
FIG. 2d is a perspective view of an alternative gasket according to the present invention.
Figure 2E:
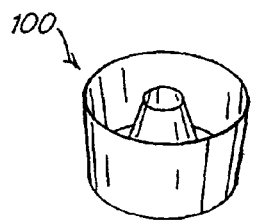
FIG. 2e is a perspective view of a second alternative gasket according to the present invention.

FIGS. 2d and 2e show other embodiments of the gasket, illustrating that the rims and base may be of differing thicknesses. The appropriate thickness depends on the pressures to be employed and on the precise configuration of the gasket 100 and the related components. In all other respects, the gaskets of FIGS. 2d and 2e are the same as the gasket of FIGS. 2a, 2b, and 2c.

Of course, the invention includes within its scope many other variations of the gasket 100. For example, the gasket 100 may have a cross-section that is taller or wider than illustrated, or in which the outer and inner rims 110, 120 are of different heights. Similarly, the channel 150 may be shallower or deeper than illustrated, its walls 152, 154 may have different and in some cases non-uniform angles of flare, and it may have a "V"-shaped or rounded bottom. The gasket 100, rather than being circular in plan, may be oval, rectangular, triangular, or have any number of other shapes. The central hole 130 may also take other shapes and sizes, depending on the nature of the handpiece supply tube 410 that it is meant to fit. In addition, the central hole 130 need be not be located in the center of the gasket 130. Also, certain embodiments may have more than one hole 130. Also, and, in some embodiments, the gasket 100 need not fully encircle the handpiece supply tube 410.

A variation on gasket 100 is illustrated in FIG. 3a, which shows an example of a non-concentric gasket that will accomplish the purposes of the invention. In this embodiment, the hole 202 is in the side of a cup-shaped gasket 200, and the hole 202 is tapered. The gasket 200 is held in a chamber 204 similar to that of previous figures, composed of a stem 208 and a cap 210 and having high pressure inlet 212. A hole 206 is provided in the chamber, in this case through the wall of the stem 208. The need to provide sufficient tapering of the gasket 200 without a significant projection may require a thicker gasket 200.

In another embodiment, as shown in FIG. 3b, a first gasket 220 has an aperture 222. The edges 224 of the first gasket 220 will seal upon a second gasket 226, which has taper in its aperture 228 to seal on a tube that is inserted through hole 230. The high pressure inlet 232 is illustrated as being non-concentric. This arrangement allows for a longer aperture 228 through the second gasket 226 to improve sealing, while maintaining the ability to injection mold the parts.

In other embodiments of the invention, it might be desirable to have more than one high pressure outlet from the chamber. In such an embodiment, two holes could be provided in the side of the gasket 200 of FIG. 3a, or in the bottom 160 of the gasket 100 of FIG. 2. In addition, a second hole in the gasket could provide a high pressure inlet, replacing the inlets 516, 212 or 232 of FIGS. 1, 3a, or 3b. Such a gasket 240 is shown in cross-section in FIG. 3c, in an embodiment having an outer rim 242 and two inner rims 244 surrounding holes 246.

FIG. 3d shows another variant of the gasket of FIG. 1, which has a shallow annular channel between the inner and outer rims 260, 262, and, as a separate variant feature, in which the gasket has a taper and fits into a tapered region of a stem 266. The width of the base 264 is reduced to an edge, or a thin rim, to prevent extrusion of the gasket around the tube when the apparatus is pressurized.

Gasket 100 is preferably made of an elastomeric plastic, although with appropriate design (e.g., the design of FIG. 2e) it could be formed of a flexible metal. The plastic should be reasonably hard; a Durometer rating of 90 (Shore A scale) has been found to be suitable, but the Durometer rating may be higher or lower, ranging, for example, from about 25 to about 100, depending on the desired pressure, the desired insertion force, and on the desired clearance between the handpiece supply tube 410 and the cap 530. The gasket 100 may be manufactured by any of the large variety of known methods for forming objects from plastic. For prototypes, machining is convenient; for production, molding is typically more cost-effective. Any plastic may potentially be of use in the invention; suitable materials include polyurethane, silicone, nylon, acetal, and rubber. Because prototyping is simple, any plastic can easily be evaluated for suitability without undue experimentation.

The gasket 100 of the illustrated embodiment is enclosed in a chamber 500, as illustrated in FIG. 1. In this embodiment, the gasket 100 is inserted into an opening 512 in a stem 510, and the chamber is completed by mounting cap 530 onto stem 510, thereby retaining the gasket 100.

Figure 4A:
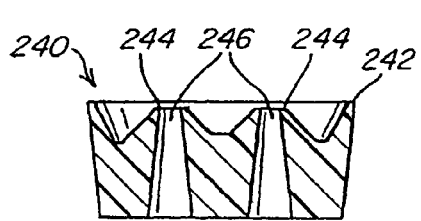
FIG. 4a is an end view of a cap according to the present invention.
Figure 4A:
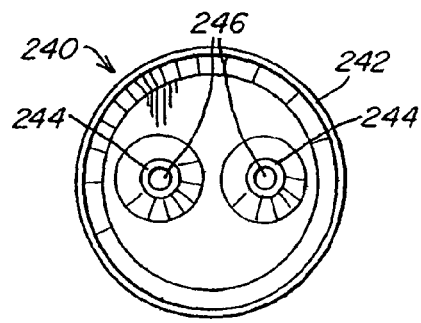
Figure 4A:
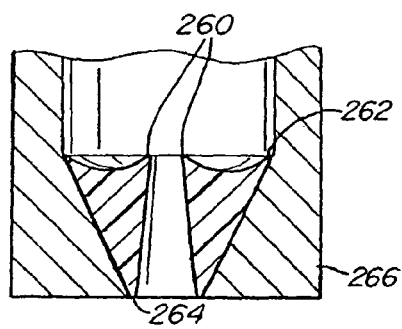
Figure 4A:
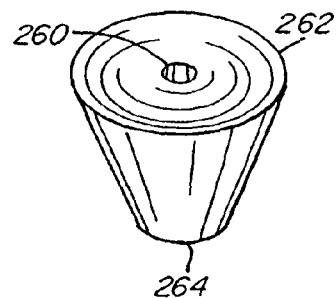
Figure 4A:
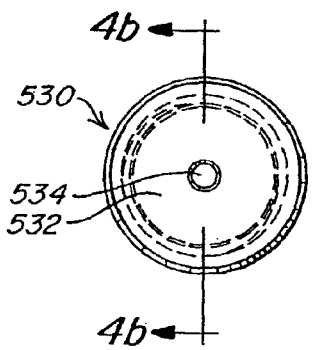
Figure 4B:
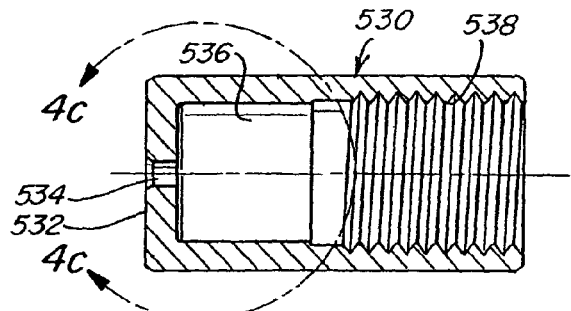
Figure 4C:
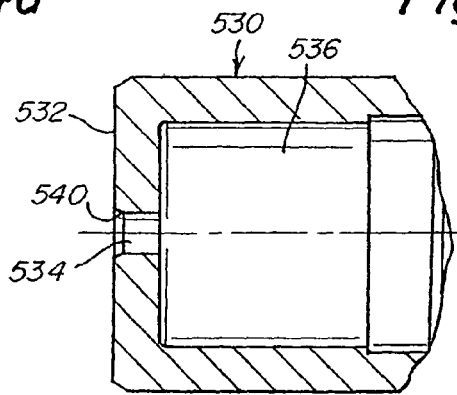
FIG. 4c is a detail of FIG. 4b.

The cap 530 is shown most clearly in FIG. 4, in which FIG. 4a shows a face-on view of the cap 530 and FIG. 4b shows a cross section of the entire cap 530. The cap 530 may be made of a metal such as stainless steel, plastic, or any other material suitable for withstanding the desired pressures. The face 532 of the cap has an aperture 534 for insertion of the handpiece supply tube 410. While the aperture 534 of the illustrated embodiment is approximately circular, it could be any suitable shape in other embodiments. The interior 536 of the cap 530 of this embodiment is hollow and, in a preferred embodiment, it carries internal screw threads 538. FIG. 4c shows a more detailed view of the face 532 of the cap 530. In particular, aperture 534 typically carries a chamfer 540 to facilitate insertion of the handpiece supply tube 410. Of course, the cap 534 need not be circular in cross-section as shown in FIG. 4, but rather can have any appropriate cross-sectional shape.

The diameter of the aperture 534 relative to the outer diameter of the handpiece supply tube 410 is not critical. There must be enough clearance to allow ready insertion of the handpiece supply tube 410 into the aperture 534 and through the gasket 100, while the upper limit of the allowable clearance is set by the need to prevent extrusion of the gasket 100 under pressure of the fluid. Clearly, harder gaskets and lower pressures permit greater clearance. As a practical matter, a minimum clearance between wall 415 and the inner surface of aperture 534 is about 0.0005 inch, a typical clearance is of about 0.001 to about 0.005 inch, and clearances up to about 0.02 inch, or more, are possible.

Figures 5A, 5B:
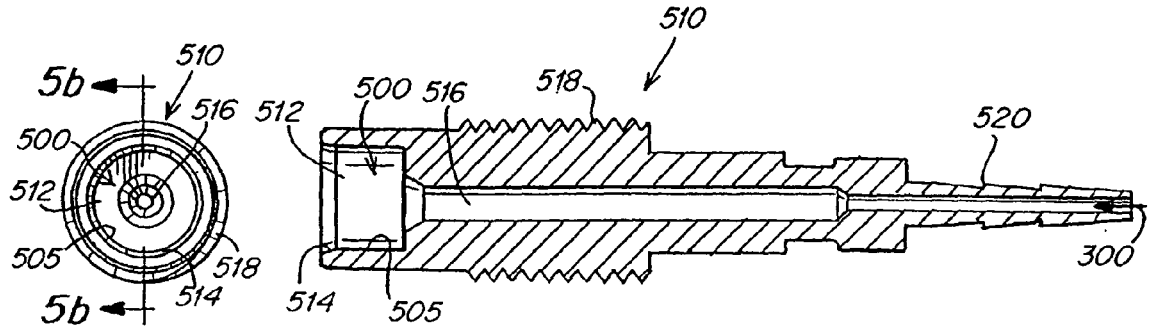

One configuration for stem 510 of this embodiment is shown in FIG. 5, in which FIG. 5a is a face-on view and FIG. 5b is a cross-section. One end of the stem 510 of this embodiment has an opening 512 for receiving gasket 100. The side wall of opening 512 forms the inner wall 505 of the chamber 500 with which the gasket 100 is in engagement under pressure. The opening 512 typically is provided with a chamfer 514 to simplify insertion of the gasket 100. A passage 516 connects the high-pressure fluid source 300 with the opening 512. In this embodiment, the central portion of the stem 510 has threads 518 on its outer surface that mate with the threads 538 on the cap 530. The other end of the stem 510 may carry a barb 520 for firmly connecting the stem 510 to the high-pressure fluid source 300. While the barb 520 of this embodiment may be connected to the stem 510 by swaging, it could be connected by gluing, welding, brazing, potting, crimping, screw connecting, clamping, or other known means of fastening a tube to a hollow object so as to allow flow through the object from the tube. In other embodiments, the barb 520 may be an integral part of the stem 510. It should be understood, however, that the method of connection of the stem 510 to the high pressure fluid source 300 is a part of the invention and may be made by any suitable means capable of withstanding the applied pressure without leaking. Like the cap 530, the stem 510 may be made of a metal such as stainless steel, plastic, or any other material suitable for withstanding the desired pressures, and it may have any appropriate cross-sectional shape.

Figure 6A:
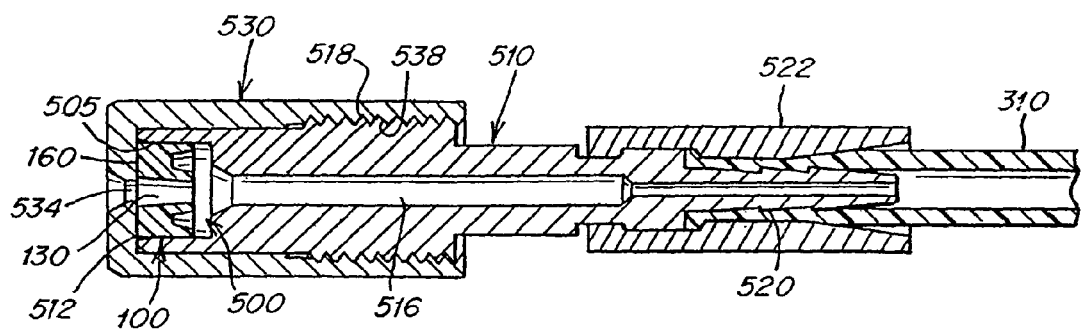
FIG. 6a is a cross-sectional view of a supply assembly according to the present invention.
Figure 6B:
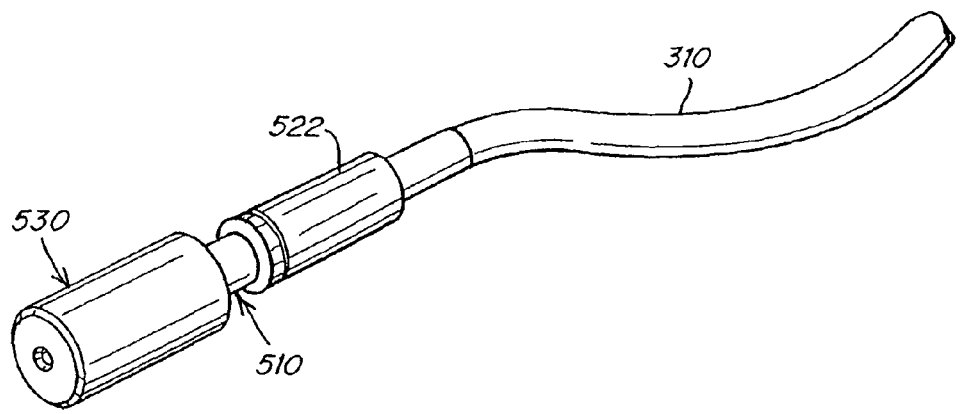
FIG. 6b is perspective view of a supply assembly according to the present invention.

FIG. 6 illustrates an assembled device in which gasket 100 resides within chamber 500. FIG. 6a is a cross-section and FIG. 6b is an exterior perspective view. In this embodiment, assembly includes inserting the gasket 100 into the opening 512 of the stem 510, such that the bottom 160 of the gasket faces outwardly and attaching the cap 530 onto the stem 510. Notably, aperture 534 is in registration with the hole 130 in the gasket 100. The connection between cap 530 and stem 510 need not be tight enough to be leakproof because the seal between the gasket 100 and the side wall 505 of the chamber 500 typically prevents fluid from reaching the region of the screw connection. FIG. 6a shows an example of a crimped seal 31 that serves to connect a high pressure hose 310 to the barb 520.

While the use of threads 518, 528 to connect the cap 530 to the stem 510 has been found to be particularly effective, other methods also may be used. In different embodiments, for example, the threaded connection between the cap 530 and the stem 510 could be replaced by a clamp, a bayonet-type connector, a weld or braze, glue or other adhesive, a press-fit, or a crimp forming a seal. Crimping and welding are preferred in production for economy and simplicity. FIG. 7a shows a crimp seal 600 that can make a leakproof connection by forcing the material of the cap 530 into a circular groove 602 in the stem 510. Such seals are themselves capable of withstanding pressures of 25,000 psi or more, although in operation a gasket (not illustrated) similar to gasket 100 could be disposed in the chamber 500. In FIG. 7b, the connection between the stem 510 and the cap 530 is made by a weld 604; again, a gasket (not shown) could be present in chamber 500. As noted, the means for connecting cap 530 to stem 510 is not important, and any connecting means can be used that provides sufficient strength to resist the pressure applied to the cap 530 when the device is pressurized. As the device may be disposable, non-reversible connecting means may be acceptable.

The invention also includes within its scope chambers 500 formed in other ways. For example, in another embodiment, as illustrated in FIG. 8a, the chamber 500 could be constructed such that the cap 530 carries the gasket 100 and screws into a stem 510. In such a design, a second gasket 606, generally similar to the gasket 100 described above, could be used to prevent leakage through the threaded connection between the cap 530 and stem 510. It should also be appreciated that, as illustrated in FIG. 8b, the chamber 500 can be "reversed," so that the chamber 500 is formed between a handpiece 400 and a cap 530 attached (by any means, such as those shown in previous figures) to the proximal end of handpiece 400. Chamber 500 contains a gasket 100, and is connected via connectors (not shown) to a source of high pressure fluid via a tube 410 inserted into the aperture 534. Moreover, in another embodiment, as shown in FIG. 8c, the chamber 500 may be double-ended and connect to both the fluid source and the handpiece 400 via tubes (not shown) through apertures 534. A body 608 with a central passage 610 carries a cap 530 having an aperture 534 on each end, to form two chambers 500, each of which contains a gasket 100. The caps 530 may be bonded to the body by any means. The bond between the cap or caps 530 and the handpiece 400 or body 608 must be watertight at high pressures (in the absence of a second gasket as in FIG. 8a), which can be accomplished by crimping or welding, among other methods, or, in some embodiments, by the provision of a second gasket similar to that shown in FIG. 8a. The arrangement of FIG. 8c is slightly more complex than that of FIG. 8a or 8b, but provides additional flexibility.

As can be seen from FIG. 1, the pressure of the fluid in the chamber 500 exerts a force on the handpiece 400 or other attached device that is proportional to the area of handpiece supply 410. In medical uses of the device, the pressures are typically in the range of about 5,000 to about 20,000 psi, although they may be lower or higher in particular procedures. The volume of fluid to be passed through the handpiece supply tube 410 is small, however, and tube 410 diameters in the range of 0.03 to 0.05 inch are generally sufficient. (The diameter of the tube 410 is not critical to the invention, and may range from about 0.001 to 0.2 or more inches.) The resulting cross-section experiences total forces (force/unit area times area) in the range of about 1 to about 100 pounds and, more commonly, about 5 to about 50 pounds. In the absence of connecting means, this force would tend to detach the handpiece 400 from stem 510 and cap 530.

Figure 9A:
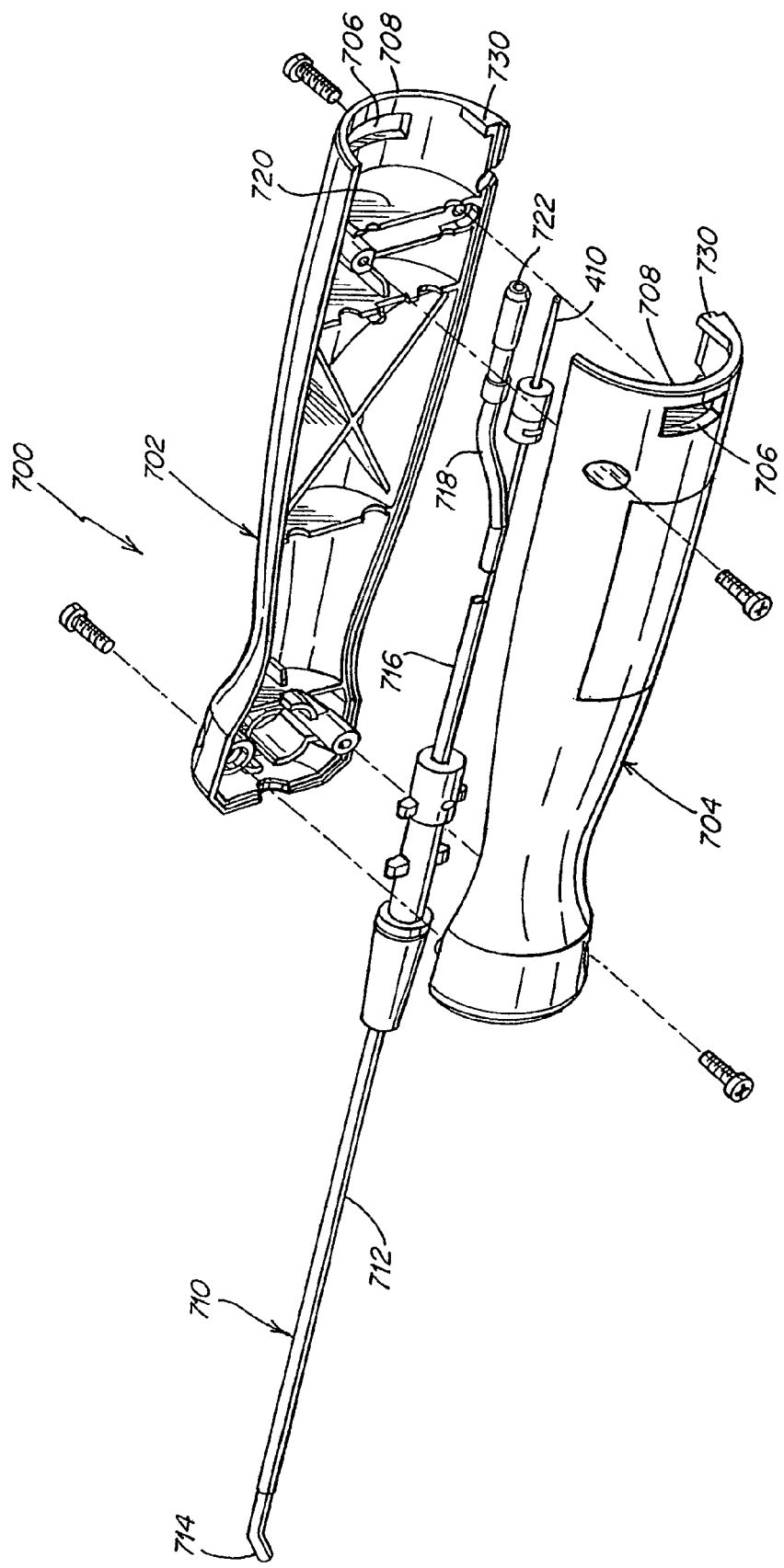
FIG. 9a is an exploded perspective view of a handpiece according to the present invention.
Figure 9B:
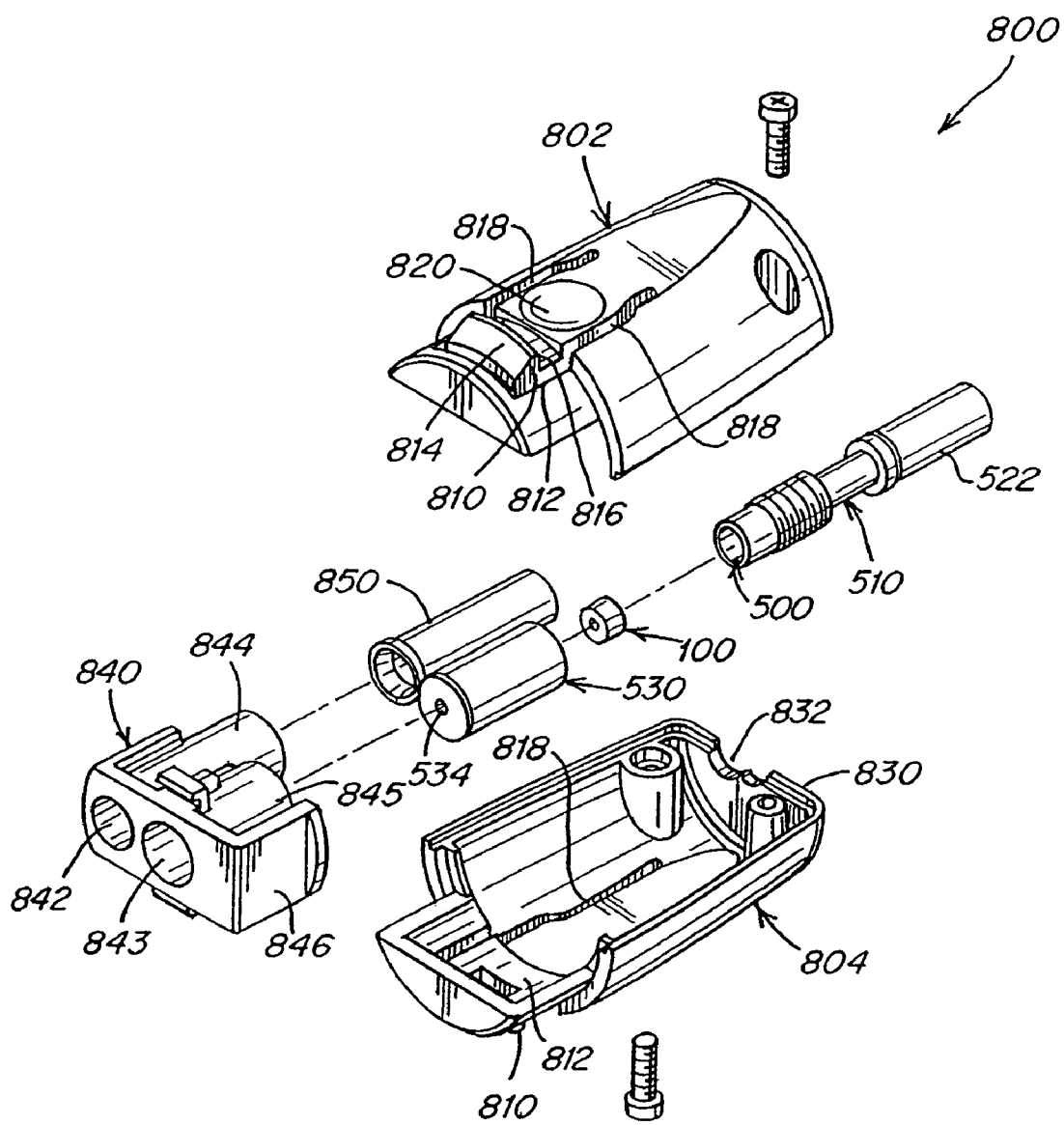
FIG. 9b is an exploded perspective view of a coupler according to the present invention.

FIGS. 9a and 9b are exploded views of a preferred embodiment of a handle 700 containing the handpiece supply tube 410 that mates with a coupler 800 that houses the chamber 500 (not shown). As shown in FIG. 9a, the handle 700 typically is assembled from two half-handles 702, 704 and, as seen in FIG. 9b, the coupler typically 800 includes two assembled half-couplers 802, 804. The particular shapes of the half-handles 702 and 704 and half-couplers 802 and 804 are not critical. Half handles 702, 704 and half couplers 802, 804 may be fixed together by any suitable means including, in this embodiment, screws. The handle 700 and the coupler 800 typically may be connected by two mirror-image, opposing moveable tabs 810 on the coupler 800 that fit into slots 706 on the handle 700. In one embodiment, tabs 810 are formed on a flexible arm 812 and have sloped distal surfaces 814 and perpendicular proximal surfaces 816. When the coupler 800 is inserted into the handle 700, the tabs 810 are depressed by the rim 708 of the handle 700 which bends the flexible arms 812. Tabs 810 then rise into the slots 706, where the tabs 810 are retained by their proximal face 816, thereby latching the tube-carrying handle 700 to the chamber-carrying coupler 800. The flexible arms 812 may be made flexible by longitudinal cuts 818 partially separating them from the rest of the coupler 800. The coupler 800 is provided with rigidity by its cylindrical shape and by a proximal face 830, which in this embodiment is solid except for openings 832, and by its connection to the handle 700.

The connection between the handle 700 and the coupler 800 may be broken by depression of the flexible arms 812, for example at pressing points 820. The exact shape and location of the pressing points 820 is not critical, although it is preferable that they have tactile features, such as reliefs, roughening, or the like, so the operator can feel where to pinch the opposing flexible arms 812. Depression of arms 812 depresses the tabs 810 below the level of the slots 706, and allows the handpiece 400 to be removed by the other hand, by lodging the handpiece 400 in a separate device (not illustrated), or even by shaking it.

While the slot and tab method of connection has been found to be effective, the means by which the handle 700 is attached to the coupler 800 is not critical to the invention, and a variety of attachment means will accomplish the desired retention. The means selected must be sufficient to withstand the applied force, and should preferably be simple, easy to operate (optionally, with one hand), and, when the handpiece 400 is a disposable item, inexpensive. In low pressure applications, the connection means may be light duty, while in other applications, more robust connection means, such as screw connectors, may be employed. In some applications, it may be desirable to connect a handpiece 400 with the use of a connector that is designed not to be releasable. Such a device is also within the scope of the invention. A number of alternative connection methods are illustrated in FIGS. 10a-e.

Figure 10A:
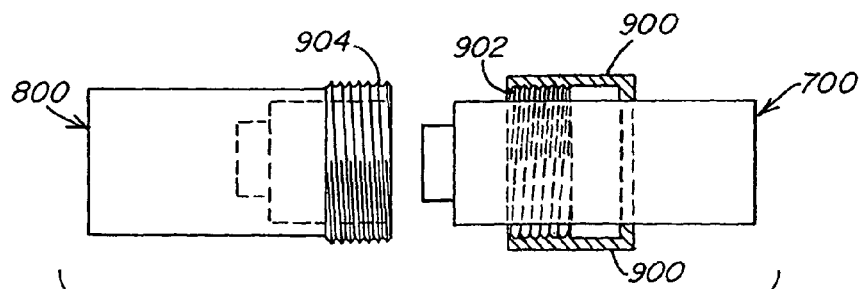
FIG. 10a illustrates a partial, side schematic diagram of an alternative means of attaching a handle to a coupler according to the present invention.

FIG. 10a shows a method of connecting a handle 700 and a coupler 800 in which the handle 700 carries a sleeve 900 that has internal threads 902. The coupler 800 of this embodiment has external threads 904 and the device is assembled by screwing the internal threads 902 onto the external threads 904.

Figure 10B:
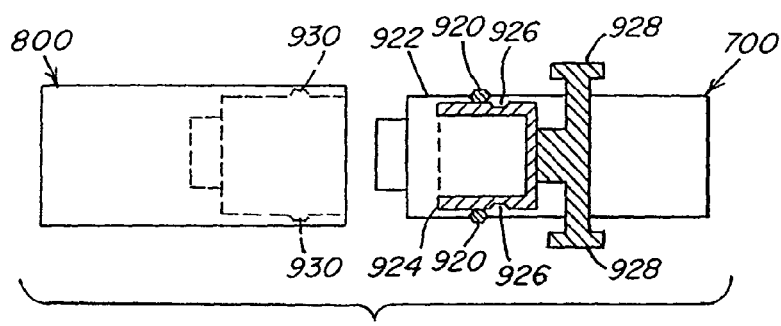
FIG. 10b illustrates a partial, side schematic diagram of a second alternative means of attaching a handle to a coupler according to the present invention.

In the embodiment of FIG. 10b, the handle 700 has balls (or rods) 920 that protrude partially through its surface 922. A sleeve 924 that has recesses 926 is attached to tabs 928. When the tabs 928 are moved in the direction of the balls 920, the sleeve 924 moves in the same direction until the balls 920 slip into the recesses 926. With the balls 920 in the recesses 926, the handle 700 may be inserted into the coupler 800, after which the tabs 928 may be returned to their original position, moving the sleeve 924 in the direction out of the coupler. As the sleeve 924 moves in that direction, it causes the balls 920 to again protrude through the surface 922 and to fit into the recesses 930, thereby retaining the handle 700 in the coupler 800. The handle 700 may be released from the coupler 800 by reversing the process.

Figure 10C:
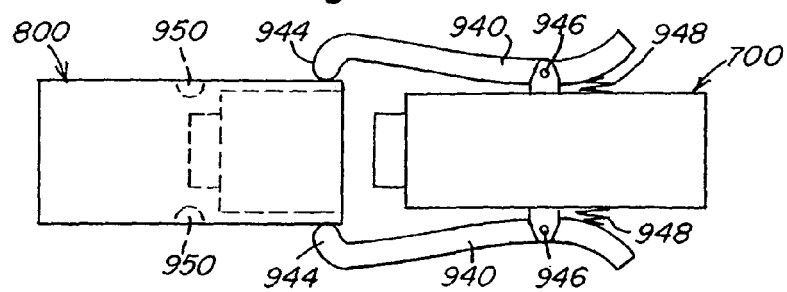
FIG. 10c illustrates a partial, side schematic diagram of a third alternative means of attaching a handle to a coupler according to the present invention.

FIG. 10c shows an embodiment which the handle 700 may be connected to coupler 800 by means of a lever-type arrangement. In this embodiment, two levers 940 are attached to the handle 700 by means of pivots 946. Springs 948 bias the ends 942 of the levers 940 away from the handle 700 about the pivot 946. The device of this embodiment is assembled by pinching the ends 942 of the levers 940 in the direction of the handle 700, which causes the jaws 944 of the levers 940 to open. After the handle 700 is inserted into the coupler 800, the ends 942 are released and the springs 948 cause the jaws 944 to close. The closed jaws 944 fit into coupler recesses 950, thereby retaining the handle 700 in the coupler 800. The handle 700 can be released by again by pinching the handle ends 942 to open the jaws 944.

Figure 10D:
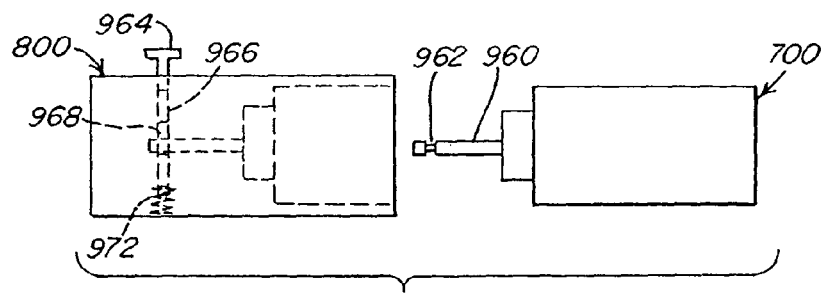
FIG. 10d illustrates a partial, side schematic diagram of a fourth alternative means of attaching a handle to a coupler according to the present invention.
Figure 10E:
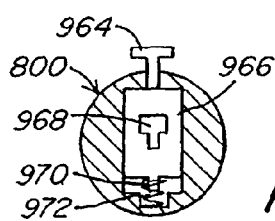
FIG. 10e is a detail of FIG. 10d.

In the embodiment of FIGS. 10d and 10e, the handle 700 carries a lock pin 960 that has a notch 962 at the end farthest from the handle 700. The coupler 800 has a finger actuator 964 attached to a plate 966 that has a keyhole opening 968, as shown in FIG. 10e. The plate 966 has a tab 970 that fits into a spring 972, which biases the plate 966 in the direction of the finger actuator 964. The device is assembled by depression of the finger actuator 964, which moves the plate 966 into a position in which the larger end of the keyhole opening 968 is approximately concentric with the coupler 800. In this position, the handle 700 can be inserted into the coupler 800, causing the lock pin 960 to pass through the larger end of the keyhole opening 968. When the force is removed from the finger actuator 964, the force of the spring 972 causes the plate 966 to move in the direction of the finger actuator 964 which, in turn, causes the smaller end of the keyhole opening 968 to slip over notch 962, thereby retaining the handle 700 in the coupler 800. The handle may be removed by depression of the finger actuator 964.

It is preferable that the high pressure source be turned off or otherwise disengaged during changing of handpieces. In addition to the creation of an undesirable spray of fluid, the insertion or withdrawal of the tube while the gasket 100 is under pressure is potentially damaging to the gasket 100. To this end, the attachment means can be designed to make it difficult to unlatch the handpiece while pressure is applied to the device. For example, referring to FIG. 9*b*, the proximal face 816 of the tab 810 can be slanted in the same direction as distal face 814, so that the handle 700 must be pushed towards the coupler 800 to permit disengagement. Other means of achieving the same function can readily be devised for other connecting systems. Alternatively or in addition, mechanical or electronic interlocks can disengage the high pressure source when the attachment means is operated.

As seen in FIG. 9*a*, handle 700 of the illustrated embodiment encloses a tube assembly 710 having a high pressure tube 702 extending from handpiece supply tube 410 to distal region 704, and a low pressure return tube 706 connected to a low pressure hose 708 and a connector 710. The handpiece supply tube 410 and the connector 710 both extend through a septum 720, and are recessed with respect to rim 708. Coupler 800 encloses the chamber 500, including cap 530, gasket 100, and stem 510, as well as tube supporting block 840 and low pressure connector 850. Tube supporting block 840 has openings 842, 843 that communicate with tubes 844, 845 into which the chamber 500 and low pressure connector 850 are inserted.

In this embodiment, the device is assembled by inserting the handle 700 into the coupler 800. In a preferred embodiment, a cutout 846 on block 840 mates with the key 730 to ensure correct orientation. The position of the handpiece supply tube 410 and the connector 710 within the handpiece also helps ensure that the coupler 800 is inserted into the handle 700 in the proper alignment and reduces the possibility that the handpiece supply tube 410 might be bent or otherwise damaged. Upon assembly, the handpiece supply tube 410 passes through opening 843, tube 845, aperture 534 of cap 530, and gasket 100. Connector 710 of low pressure hose 708 passes through opening 842 and tube 844 and mates with connector 850. As described above, the attachment means secures handle 700 to the coupler 800.

The operation of this illustrative embodiment may be appreciated by reference to FIGS. 1 and 9. Upon activation of the high pressure fluid source, fluid is channeled through the fluid passage 516 and into the chamber 500. When the high pressure fluid is received into the chamber 500, the pressure forces the inner rim 120 against wall 415 of handpiece supply tube 410, the outer rim 110 against the inner wall 505, and the base 140 of the gasket 100 against the cap 530. The force pressing the inner rim 120 against wall 415 of the handpiece supply tube 410 and outer rim 110 against the inner wall 505 of the chamber 500 increases as the pressure of the fluid increases. The fluid cannot escape from the chamber 500 by running along wall 415 of the handpiece supply tube 410, because of the tight seal between the inner rim 120 and wall 415, nor can it reach the threads 518, 538 between the stem 510 and the cap 530, because of the seal between the outer rim 110 against the inner wall 505. Having no other outlet, the fluid travels through the tube assembly 710 and is emitted from the distal region 704 tip at high pressure, providing a tissue cutting action. The spent fluid is then drawn into the low pressure return tube 706, travels through the low pressure hose 708, and is ultimately collected for disposal.

While the invention has been described in conjunction with specific embodiments, many alternatives, modifications, and variations will be apparent to those skilled in the art. Accordingly, embodiments set forth herein are intended to be illustrative of the various aspects of the invention, not limiting, and various changes may be made without departing from the spirit and scope of the invention. It should also be appreciated that this system does not significantly change the design of the handpiece, other than to require a chamber or a tube and a latch or other connector, so any of the known handpiece types for using high pressure fluids in medical and other procedures can be connected by means of this connecting system. The handpieces themselves may have further interchangeable features, which may also make use of the connection system of the invention.

What is claimed is:

1. A medical device having a high pressure fluid connection comprising:
    a first lumen adapted for fluid flow at a high pressure;
    a second lumen adapted for fluid flow and arranged at least partially within the first lumen; and
    a gasket positioned between the first lumen and the second lumen and constructed and arranged to create fluid impermeable seals between the gasket and the first lumen and between the gasket and the second lumen when the high pressure fluid flowing through the first lumen exerts a force upon the gasket.

2. The medical device of claim 1, wherein the pressure of the fluid flowing though the connection seals the gasket against an inside surface of the first lumen and against an outside surface of the second lumen.

3. The medical device of claim 1, wherein the gasket is maintained in its longitudinal position by a cap.

4. The medical device of claim 1, wherein the force resulting from the pressure on the gasket has a component that is normal to the axis of at least one of the first and second lumens.

5. The medical device of claim 1, wherein the gasket has a top surface facing in a direction upstream of the fluid flowing through the connection and the top surface contains a channel.

6. The medical device of claim 5, wherein the channel has an open top and a closed bottom and at least part of the open top is wider than at least part of the closed bottom.

7. The medical device of claim 1, wherein the first and second lumens are concentric to each other.

8. A medical device having a quickly changeable connection between a high pressure fluid source and a hand piece, wherein the connection comprises:
    a thin tube having a lumen in fluid connection with a first fluid pathway extending through the hand piece;
    a chamber, the chamber having a first opening receiving the thin tube and a second opening in fluid connection with a second high pressure fluid pathway;
    a gasket in the chamber, the gasket having a base disposed adjacent to the first opening, and a passage through the base surrounding the thin tube, wherein the gasket has a first rim contacting the wall of the chamber and a second rim contacting the thin tube; and
    a latching mechanism to maintain the tube in the gasket.

9. The medical device of claim 8, wherein the chamber is formed by a cap and a stem.

10. The medical device of claim 8, wherein the gasket has a Durometer rating in the range of about 45 to about 95.

11. The medical device of claim 8, wherein at least one of the rims of the gasket projects in a radial direction.

12. The medical device of claim 8, wherein the assembled device can withstand a pressure of at least about 5,000 psi without leaking.

13. The medical device of claim 8, wherein the assembled device can withstand a pressure of at least about 10,000 psi without leaking.

14. The medical device of claim 8, wherein the assembled device can withstand a pressure of at least 20,000 psi without leaking.

15. The medical device of claim 8; wherein each of the components of the device is sterile.

16. The medical device of claim 8, wherein the fluid is a liquid.

17. The medical device of claim 16, wherein the liquid is sterile.

18. The medical device of claim 8, wherein the fluid flows from the high pressure fluid source to the hand piece through the connection.

19. The medical device of claim 8, wherein the fluid flowing through the hand piece forms a fluid jet that is used for at least one of cutting tissue, debriding wounds, lavage, disinfection, washing of tissue surfaces and providing driving power to devices.

20. A system for quickly changing hand pieces attached to a high pressure fluid source; the system comprising:
- at least one hand piece carrying a portion of a latching mechanism and one of a connecting tube and a chamber having an aperture leading to a gasket;
- a high pressure fluid source carrying a complementary portion of a latching mechanism and the other of a connecting tube and a chamber having an aperture leading to a gasket;
- wherein the gasket has an inner rim and an outer rim and the inner and outer rims engage the connecting tube and the wall of the chamber, respectively, when the connecting tube is inserted in the chamber; and
- wherein the gasket is configured to create a fluid impermeable seal between the gasket and the connecting tube when the high pressure fluid applies pressure to the gasket.

21. A gasket for a high-pressure connector in a surgical instrument or system, the gasket comprising:
- an annular member for surrounding a high pressure tube admitted into a chamber;
- an inner rim on the annular member that seals tightly against the high pressure tube when pressure is applied to the chamber; and
- an outer rim on the annular member that seals tightly against an inner wall of the chamber when pressure is applied to the chamber.

\* \* \* \* \*